(12) United States Patent
Buri et al.

(10) Patent No.: US 9,556,320 B2
(45) Date of Patent: Jan. 31, 2017

(54) PROCESS FOR WATER BASED MINERAL MATERIAL SLURRY SURFACE WHITENING

(75) Inventors: Matthias Buri, Rothrist (CH); Samuel Rentsch, Aarburg (CH); Claudia Pudack, Zürich (CH)

(73) Assignee: Omya International AG, Oftringen (CH)

( * ) Notice: Subject to any disclaimer, the term of this patent is extended or adjusted under 35 U.S.C. 154(b) by 199 days.

(21) Appl. No.: 13/996,719

(22) PCT Filed: Dec. 22, 2011

(86) PCT No.: PCT/EP2011/073801
§ 371 (c)(1),
(2), (4) Date: Aug. 23, 2013

(87) PCT Pub. No.: WO2012/093039
PCT Pub. Date: Jul. 12, 2012

(65) Prior Publication Data
US 2014/0290536 A1   Oct. 2, 2014

(30) Foreign Application Priority Data
Jan. 7, 2011   (WO) ................ PCT/EP2011/050187

(51) Int. Cl.
| | | |
|---|---|---|
| C08K 3/26 | (2006.01) | |
| C08K 3/00 | (2006.01) | |
| C09C 1/02 | (2006.01) | |
| C09C 1/36 | (2006.01) | |
| C09C 1/40 | (2006.01) | |
| C09C 1/42 | (2006.01) | |
| C09C 3/10 | (2006.01) | |
| D21H 17/00 | (2006.01) | |
| G01N 21/25 | (2006.01) | |
| C08L 33/02 | (2006.01) | |
| G06K 9/62 | (2006.01) | |

(52) U.S. Cl.
CPC .............. *C08K 3/0033* (2013.01); *C08K 3/26* (2013.01); *C08L 33/02* (2013.01); *C09C 1/021* (2013.01); *C09C 1/3676* (2013.01); *C09C 1/405* (2013.01); *C09C 1/407* (2013.01); *C09C 1/42* (2013.01); *C09C 3/10* (2013.01); *D21H 17/00* (2013.01); *G01N 21/25* (2013.01); *G06K 9/6202* (2013.01); *C01P 2004/62* (2013.01); *C01P 2006/12* (2013.01); *C01P 2006/60* (2013.01); *C01P 2006/62* (2013.01); *C08K 2003/265* (2013.01)

(58) Field of Classification Search
CPC .......... C09C 3/10; C09C 1/0121; C09C 1/405; C09C 1/407; C09C 1/42; C08L 33/02; C08K 3/0033; C08K 3/26; C08C 1/3676; D21H 17/00
See application file for complete search history.

(56) References Cited

U.S. PATENT DOCUMENTS

| | | |
|---|---|---|
| 2002/0051097 A1 | 5/2002 | Caisey-Bluteau et al. |
| 2003/0202929 A1 | 10/2003 | Golley |
| 2009/0312459 A1 | 12/2009 | Gane et al. |
| 2010/0219269 A1 | 9/2010 | Husband et al. |
| 2012/0077917 A1 | 3/2012 | Gane et al. |

FOREIGN PATENT DOCUMENTS

| | | |
|---|---|---|
| EP | 2000213 A1 | 12/2008 |
| WO | 9744642 A2 | 11/1997 |
| WO | 0129125 A1 | 4/2001 |
| WO | 2004026973 A1 | 4/2004 |
| WO | 2008124178 A1 | 10/2008 |

OTHER PUBLICATIONS

Wallqvist et al. Influence of Wetting and Dispersing Agents on the Interaction between Talc and Hydrophobic Particles. Langmuir 2009, 25(12), 6909-6915.*
Product Sheet Nippon Denshoku: PF-10R Spectrophotometer for Pater, Jun. 22, 2011.
International Search Report, dated Jun. 3, 2012 for PCT Application No. PCT/EP2011/073801.
Written Opinion of the International Searching Authority, dated Jun. 3, 2012 for PCT Application No. PCT/EP2011/073801.

* cited by examiner

*Primary Examiner* — John Uselding
(74) *Attorney, Agent, or Firm* — Amster, Rothstein & Ebenstein LLP

(57) ABSTRACT

The present invention is directed to a process for surface whitening mineral matter in a slurry that includes the following steps: (a) preparing by dispersing and/or grinding at least one water based mineral matter slurry; and (b) adding during and/or after step a) 0.005 wt % to 0.5 wt %, based on dry weight of the mineral matter, of at least one alkylene oxide block co-polymer or at least one alkylene oxide random co-polymer.

30 Claims, No Drawings

PROCESS FOR WATER BASED MINERAL MATERIAL SLURRY SURFACE WHITENING

CROSS-REFERENCE TO RELATED APPLICATIONS

This application is a U.S. national phase of PCT Application No. PCT/EP2011/073801, filed Dec. 22, 2011, which claims priority to PCT Application No. PCT/EP2011/050187, filed Jan. 7, 2011.

The process relates to mineral material slurries used in concrete, sealants, paper, paint or plastic applications. Especially natural, ground calcium carbonate slurry is used in paint and paper industry as filler or coating pigment. Natural sources of such pigments include traces of coloured impurities, such as oxides, e.g. iron oxide, sulphides, such as iron sulphide, silicates, such as feldspars and mica but also carbon sources, such as crystalline and/or amorphous carbon, for example graphite.

The problem the printing and plastics industry faces today is often a slight gray or dark veil-like appearance on the slurry surface coming from small traces of coloured impurities, for example graphite as mentioned above.

If natural ground minerals are brought into a water based slurry form, for example under stirring and the addition of a dispersant, often a gray or dark veil-like appearance on the surface is observed, said dark veil-like appearance originating from the flotation of traces of dark impurities of the natural minerals, for example low traces of graphite. Especially graphite and sulphides are concentrated by froth flotation on the slurry surface by only some amount of air introduced during stirring, pumping, loading or unloading.

One drawback of such white mineral slurry having gray to black veil on its surface is that it is visibly unattractive for a user. Another drawback is that such traces of impurities can form agglomerates on the slurry surface causing later on severe quality problems such as visible marking, including black stripes, in further applications, such as wall painting or paper coating. Thus, the problem to be solved by the present invention is to increase the surface whitening of water based mineral matter slurries.

With regard to known processes performed on mineral-comprising materials and a glycol polymer featuring a somewhat high molecular weight (Mw), the skilled man is aware of WO 2005/071003, which discloses a calcium carbonate core at least partially covered with a coating added via two distinct consecutive steps, each step using a different coating. However, not only is the goal of this invention entirely different from that of the present invention, namely to provide calcium carbonate particles with improved dispersibility and a lower agglomeration tendency, but this application mentions only a general polyhydric alcohol that may constitute the first and/or second coating material. Additionally, while a single, brief mention is made that these coatings may be introduced by a grinding process, no aspect of such process is either described or exemplified.

US 2002/0004541 relates to low pour point ethylene oxide/propylene oxide block copolymer surfactants, and a process for preparing the same. The object of the invention, which is again entirely outside of that of the present invention, is achieved by combining the indicated copolymer with low molecular weight glycol, water and a dialkyl sulfosuccinate. It is further described that such block copolymers may be used as grinding aids, however no indication is provided as to the nature of the material ground, whether this grinding is wet or dry, nor the efficiency of the grinding process.

US 2005/0107493 discloses a method for producing coated, fine-particle inorganic solids, the surface of which is coated with fine inorganic solid particles, which may be carbonates, containing at least two different organic additives. It is indicated that the second additive may be a polyethylene glycol. It is possible to carry out the modification, which may take place via a grinding process. However, again, no information is provided regarding the grinding efficiency, nor is a dry grinding process exemplified or discussed in any detail. Furthermore, the goal of the invention is entirely different from that of the present invention, namely to obtain a uniform distribution of the additives over the solid surface.

DE 102005043542 discloses an aqueous graphite dispersion including graphite particles dispersed in water along with stabilizers acting as dispersants, and additives. The graphite particles are at least partially spherical. Polyethylene glycol is described, for example, as a good dispersant. However this does not provide a solution to increase the surface whitening of mineral material slurries, as polyethylene glycol works as a collector in this environment, which finally will lead to a darkening of the slurry surface.

In order to prevent such slurry surface darkening, the skilled man is therefore faced with the following technical problem: to remove the concentrated dark material/materials from the slurry surface via an expensive flotation process, resulting in product loss and waste material deposit.

Thus the prior art does not provide for a teaching to the skilled man to arrive at the solution of the present invention, nor had the objective reason to search for a solution in these domains, and further, even had he done so, he would not have located any document therein addressing the same or even a similar technical problem to that he was seeking to resolve.

This means, that the industry, after all, is still interested to improve the processes known in the art by reducing or eliminating such waste material in a simple and low energy consuming process.

In response to those needs in the industry, the applicant has surprisingly found a process using a selective group of additives to prevent flotation of coloured mineral matter to the surface of white mineral matter slurries and thereby increasing the whitening of the mineral matter slurry surface.

A further advantage of the process of the present invention is, that no or only very little waste material is produced by the inventive process.

A further aspect of the present invention is that the product produced by the inventive process does not provoke dark stripes during wall painting or paper coating by formed agglomerates and/or aggregates on the mineral matter slurry surface.

A further problem to solve is the whiteness measurement of liquid slurry surface. Whiteness measurement of liquid slurry surface is not possible with today's common equipment such as Elrepho powder whiteness measurement instruments.

Surprisingly it was found that the whiteness of a digitalized picture of the slurry surface, gives reproductive, comparable figures of whiteness of liquid slurry surface. As "zero whiteness" a digitalized picture with closed objective was made. For 100% whiteness a digitalized picture of $BaSO_4$ standard (the same as used in Elrepho whiteness measurement), was made. All pictures were transferred electronically to a computer software program to calculate the slurry surface wet colour or gray shade.

The process of whitening of mineral matter slurry surface is characterised in that said process comprises the following process steps:
(a) preparing by dispersing and/or grinding at least one water based mineral matter slurry,
(b) adding during and/or after step a) 0.005 wt % to 0.5 wt % in respect to dry mineral matter of at least one alkylene oxide block or random co-polymer, preferably a block-copolymer,
(c) optionally adding 0.005 wt % to 5 wt % in respect to dry mineral matter of at least one dispersing and/or grinding aid during and/or after step (a) and/or step (b).

Within the context of the present invention, grinding or grinding process shall be understood as a synonym for milling or milling process, which may also be autogenous.

The mineral matter used in the process of the present invention can be chosen from kaolin, natural or precipitated calcium carbonates, talc, mica, dolomite, bentonite, $TiO_2$, $Al(OH)_3$, or mixtures thereof. Preferably the calcium carbonate is natural calcium carbonate, such as marble, limestone, chalk, calcite or mixtures thereof. If precipitated calcium carbonate (PCC) is used, it is preferably selected from the group comprising calcitic PCC, vateritic PCC, aragonitic PCC, and mixtures thereof. In general, the mineral matter suitable to be used in the process of the present invention comprises dark hydrophobic impurities. Such impurities can be $FeS_2$ (Pyrite) or graphite or mixtures thereof but are not limited to these.

Thus, in a preferred embodiment, the water based slurry obtained by the process of the present invention is a mineral matter slurry, wherein the mineral matter is calcium carbonate, preferably natural calcium carbonate, such as marble, limestone, chalk or calcite and/or mixtures thereof.

The water based mineral matter slurry used in the process of the present invention is prepared either by dry grinding of mineral matter until the mineral matter has a $d_{50}$ from about 0.2 µm to about 100 µm, preferably from about 0.3 µm to about 50 µm, more preferably from about 0.5 µm to about 30 µm, and most preferably from about 1 µm to about 2 µm. Said dry ground mineral matter is provided in an aqueous suspension of water in amounts of up to 20 wt %, preferably up to 30 wt %, more preferably up to 40 wt % in respect to dry mineral material.

Alternatively said dry ground mineral matter is further subjected to wet grinding until the $d_{50}$ is in the range of about 0.2 µm to about 10 µm, preferably in the range from about 0.3 µm to about 5 µm, most preferably in the range from about 0.5 µm to about 2 µm.

The wet grinding is done in a range from about 5 wt % to about 80 wt %, preferably in a range from about 30 wt % to about 75 wt %, more preferably in a range from about 40 wt % to about 70 wt %, most preferably from about 50 wt % to about 60 wt % solids with respect to dry mineral matter in water in a mill.

Said milling process can be carried out batch wise or continuously. Beads suitable for milling said mineral material are known to the skilled person, such as exemplified but not limited to zircon silicate beads in the range of from 0.2 mm to 4 mm, in particular in the range from 1 mm to 1.5 mm. The milling may also be autogenous.

The water based mineral matter slurry used in the process of the present invention optionally comprises at least one anionic dispersant or grinding aid. Said anionic dispersing and/or grinding aids are organic or inorganic dispersing and/or grinding aids. The organic dispersing and/or grinding aid can be selected from citrate, maleate, fumarate, itaconate, polyacrylates and homo- or copolymers of acrylic- or methacrylic acid and combinations thereof. The inorganic dispersing and/or grinding aid is selected from pyrophosphate or polyphosphates such as hexametaphosphate, tripolyphosphate, ammonium zirconium carbonate or potassium zirconium carbonate.

The dispersant is partially or fully neutralized by at least one mono- and/or bivalent and/or trivalent and/or tetravalent neutralizing agent.

Within the context of the present invention partially neutralized means that the at least one anionic polymeric dispersant is up to 100 mol % neutralized, by at least one mono and/or bivalent neutralizing agent. For example the at least one anionic polymeric dispersant may be neutralized at a level of from 90%, or 80%, or 70%, or 60%, or 50%, or 40%, or 30%, or 20%, or 10% to about 10%, or 20%, or 30% or 40%, or 50%, or 60%, or 70% or 80%, or 90% by at least one mono- and/or bivalent and/or trivalent neutralizing agent. The at least one mono- or bivalent neutralizing agent can be chosen from alkali or earth alkali metal ions and or their salts, such as lithium, sodium, potassium, magnesium, calcium, ammonium and combinations thereof. Further suitable grades of neutralisation of dispersant are also known from FR2683537 and FR2683538.

Therefore the previously mentioned anionic dispersing and/or grinding aids can also be selected amongst polymers of sodium citrate sodium maleate, sodium fumarate, sodium itaconate, and homo- or copolymers of sodium acrylate or sodium methacrylate and combinations thereof, as well as from sodium pyrophosphate or sodium polyphosphates such as sodium hexametaphosphate, or sodium tripolyphosphate. Potassium-Zirconium calcium carbonate (KZC) or Ammonium Zirconium Calcium carbonate (AZC) might be present additionally.

The at least one anionic polymeric dispersant as disclosed herein can be chosen, for example, from polymeric dispersants comprising at least one group chosen form a hydroxyl group, an amido group, a carboxyl group, a sulfo group and a phosphono group, and alkali metal and ammonium salts thereof. For example partially or totally alkali or earth alkali neutralized polymers of acrylic or methacrylic acid or copolymers of acrylic or methacrylic acid with an alkyl acrylate or an alkyl methacrylate, or a (meth)acrylic anhydride, acrylamido-2-methyl-2-propanesulfonic acid, polyacrylamide, or acrylamine. Further suitable anionic polymeric dispersant are known from WO 2005/063371.

Particularly suitable anionic homo or co-polymeric dispersing agents and their partial or complete neutralisation are further described in FR 2 539 137 A1, FR 2 683 536 A1, FR 2 683 537 A1, FR 2 683 538 A1, FR 2 683 539 A1 et FR 2 802 830 A1, FR 2 818 165 A1, EP 0850 685 A1, FR 2 903 618 A1, FR 2 940 141, and WO 2010/063757.

The polymeric acrylic dispersants can have a weight average molecular weight (Mw) of for example, from about 1000 g/mol to 30000 g/mol, preferably from about 1300 g/mol to 20000 g/mol, more preferably from about 1500 g/mol to 17000 g/mol, still more preferably from about 2500 g/mol to 16000 g/mol, still more preferably from about 3100 g/mol to 15000 g/mol, still more preferably from about 3200 g/mol to 13000 g/mol, still further preferably in the range from about 3300 g/mol to 7500 g/mol, still further preferably in the range from about 3500 g/mol to about 6000 g/mol. Yet another range is from about 1800 g/mol to about 4800 g/mol. Particularly, suitable polymeric dispersant of the above claimed ranges are polyacrylic dispersants.

All weight molecular weights (Mw), number molecular weights (Mn) and corresponding polydispersity of the different acrylic polymers are measured as 100 mol % sodium salt at pH 8 according to an aqueous Gel Permeation Chromatography (GPC) method calibrated with a series of five sodium polyacrylate standards supplied by Polymer Standard Service with references PSS-PAA 18 K, PSS-PAA 8K, PSS-PAA 5K, PSS-PAA 4K and PSS-PAA 3K.

All weight molecular weights (Mw), number molecular weights (Mn) and corresponding polydispersity of the different alkyloxy polymers are measured at pH 8 according to an aqueous Gel Permeation Chromatography (GPC) method calibrated with a series of different polyethylene glycols. Polyethylene glycol standard, analytical standard set $M_p$ 400-40000 from Fluka (product number 81396).

The dispersant suitable for the preparation of the water based mineral slurry from the grinding processes described above, is a sodium/calcium polyacrylate having a molecular weight (Mw) in the range from about 2000 g/mol to 30000 g/mol, preferably in the range from about 3000 g/mol to 20000 g/mol, most preferably in the range from about 4000 g/mol to 10000 g/mol, still further preferably in the range from about 5000 g/mol to 9000 g/mol, and a polydispersity index PDI in the range from about 1.2 to 5.0, preferably from about 1.5 to 3.0, most preferably from about 1.8 to 2.7, the solids content is 1 wt % to 100 wt % preferably in the range from about 30 wt %-45 wt %.

The polyacrylate being present in the aqueous mineral matter slurry is in the range from about 0.01 wt % to 2 wt %, preferably in the range from about 0.1 wt % to 1.5 wt %, more preferably in the range from about 0.15 wt % to 1.2 wt % solids with respect to dry mineral matter depending on solids of the aqueous mineral matter slurry and fineness and specific surface of the mineral matter particles.

The alkylene oxide block or random co-polymer of the present invention are ethylene oxide and/or propylene oxide or butylene oxide block co-polymers; or propylene oxide and/or ethylene oxide or butylene oxide block co-polymers; or ethylene oxide and propylene oxide and ethylene oxide, or propylene oxide and ethylene oxide and propylene oxide block co-polymer, or random co-polymers of ethylene oxide with propylene oxide or butylene oxide. Further, also combinations of the above mentioned polymers are suitable to carry out the present invention.

Such block copolymers being also denoted as tri-block or bi-block copolymers such as EO/PO/EO, wherein the propylene oxide units are located between two ethylene oxide units, or vice versa such as PO/EO/PO, wherein the ethylene oxide units are located between two propylene oxide units, or EO/PO or PO/EO, their synthesis being amply described in the prior art.

The block copolymers of the present invention having the general structure

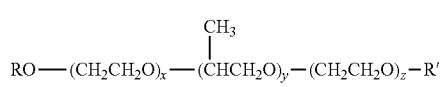

(I)

and wherein x, y, and z may each independently represent any single integer between, or equal to 1 and 120, preferably between, or equal to 1 and 80, more preferably between, or equal to 3 and 70, still more preferably between, or equal to 5 and 34, and wherein x and z are the same or different integer(s), or

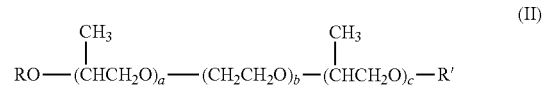

(II)

in which a, b, or c may each independently represent any single integer between, or equal to, 1 and 120, preferably between, or equal to, 1 and 80, more preferably between, or equal to, 3 and 70, still more preferably between, or equal to, 5 and 34, and wherein a and c are the same or different integer(s), or

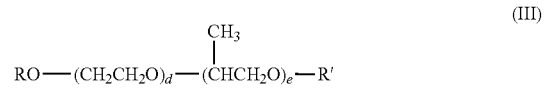

(III)

or

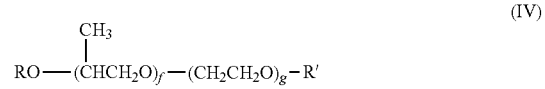

(IV)

wherein d, e, for g may each independently represent any single integer between, or equal, to 1 and 120, preferably between, or equal to 1 and 80, more preferably between, or equal to 2 and 70, still more preferably between, or equal to 4 and 40, and wherein d and e are the same or different integer(s), as well as for g being the same or different integer(s).

R and R' in the formulae mentioned above may represent alkyl residues and/or hydrogen.

Such block copolymers being also denoted as EO/PO/EO or triblock copolymers, thus propylene oxide units located between two ethylene oxide units, or vice versa, PO/EO/PO, wherein an ethylene oxide unit is located between two propylene oxide units, or EO/PO or PO/EO, their synthesis being amply described in the prior art.

The ethylene oxides, or propylene oxides, also denoted as polyethylene glycols or polypropylene glycols, the abbreviations being PEG, or PPG. Polyethylene glycol of a certain molecular weight will thus be indicated as PEG[250], which means a polyethylene glycol having a molar mass of 250 g/mol. Thus the block copolymers of the present invention for sake of simplicity may be denoted also the following way:

PEG[44-3'520]-PPG[58-4'640]-PEG[44-3'520]

wherein, according to the naming convention mentioned above, the PEG units left and right of the PPG units may be of equal or non-equal molecular weight, the molecular weight being however within the range 44-3'520 g/mol for the PEG units, and 58-4'640 g/mol for the PPG units.

A further arrangement of block copolymer is:

PPG[58-4'640]-PEG[44-3'520]-PPG[58-4'640]

or

PPG[58-4'640]-PEG[44-3'520]

or

PEG[44-3'520]-PPG[58-4'640]

Still further arrangements of block copolymers within the spirit of the present invention are block copolymers being structured the following way: PPG-PEG-PPG-PEG or PPG-PEG-PPG-PEG-PPG, or PEG-PPG-PEG-PPE, and further permutations the skilled person can readily derive thereof, or multiples thereof such as (PPG-PEG)$_i$, or (PEG-PPG)$_j$, or (PPG-PPG-PEG)$_k$ or (PPG-PEG-PPG)$_l$ or (PEG-PPG-PPG)$_m$, or (PPG-PEG-PEG)$_n$ or (PEG-PPG-PEG)$_o$ or (PEG-PEG-PPG)$_p$ or (PPG-PPG-PEG-PEG)$_q$ or (PPG-PEG-PPG-PEG)$_r$, or (PEG-PEG-PPG-PPG)$_s$ or (PEG-PPG-PEG-PPG)$_t$ or (PPG-PEG-PEG-PPG)$_u$ or (PEG-PPG-PPG-PEG)$_v$, and/or other possible permutation the skilled person can readily derive from, for example one PGG unit with three PEG units or one PEG unit with three PPG units, wherein the PPG and/or PPE units have the same molecular weight, or different, or the PPG's have the same molecular weight whereas the PEG are different or vice versa, and wherein i, j, k, l, m, n, o, p, q, r, s, t, u, v, w, represent any single integer number between, or equal to, 1 and 120, preferably between, or equal to, 5 and 100, more preferably between, or equal to, 10 and 80, still more preferably between, or equal to, 25 and 70, most preferably between or equal to 30 and 60, especially between and equal to 40 and 50.

Within the context of the present invention, any single integer between, or equal to, 1 and 120, means, 1, 2, 3, 4, 5, 6, 7, . . . 20, 21, . . . 30, 31, . . . 40, 41, . . . 50, 51, . . . 60, 61, . . . 70, 71, . . . 80, 81, . . . 90, 91, . . . 100, 101, . . . 110, 111, . . . 120.

The skilled person will also recognize that the propylene oxide unit can be replaced with structurally related alkylene oxides, such as butylene oxide, or other alkylene oxides with carbon atom backbones containing C5, C6, C7, C8, C9, C10 or more carbon atoms, said carbon atom backbones being further branched or not. As it will be recognized by the skilled person, not only the propylene oxide units can be replaced with the alkylene oxides mentioned before, but also the ethylene oxide units.

Particular representatives of such alkylene oxide block copolymers are, but not limited to: Triblock PEG[250]-PPG[1800]-PEG[250] (31PO/11EO, wherein 31PO refers to 31 propylene oxide units, and 11EO refers to 11 ethylene oxide units), Dowfax 63N30, Dowfax 63N40, both being linear EO/PO block copolymers from *The Dow Chemical Company* Lumiten P-T, an EO/PO block copolymer from BASF triblock PEG[300]-PPG[1200]-PEG[300], triblock PPG[2100]-PEG[600]-PPG[2100], or blends of the same. Such blends are in the ratio range of from about 1:100 (w/w) to 100:1 (w/w), preferably in the range from about 1:50 (w/w) to 50:1 (w/w), more preferably in the range from about 1:30 (w/w) to 30:1 (w/w), most preferably in the range from about 1:10 (w/w) to about 10:1 (w/w). Still further ranges are from about 1:5 (w/w) to about 5:1 (w/w), preferably from about 1:3 (w/w) to about 3:1 (w/w), more preferably from about 1:2 (w/w) to about 2:1 (w/w): a particular blend being 1:1 (w/w). It is evident to the skilled person that such blends can not only be made out of two of the above mentioned components but from more, such as blending at least three or more of the alkylene oxides mentioned above, and ranges of the at least three blended alkylene oxides, would lie in ranges of from 1: (100-1) for each of the at least three alkylene oxides.

Within the context of the present invention, triblock copolymers refer to polymerization products of alkylene oxides of different classes as previously mentioned. The polymerisation processes employed being well known to the skilled person.

Further to this, the alkylene oxides mentioned above can also be combined with still other alkylene oxides, such as Bevaloid 2565, a propylene oxide ethylene oxide block copolymer from *Kemira Chimie SA*. A particular preferred combination but not limited to is Lumiten-P-T/Bevaloid 2565 (2:1 w/w).

The alkylene oxides of the present invention can be employed in the mineral matter slurries as a single component, or as a preformulated blend or added in serial order during or after the milling process.

The employed total amount of the alkylene oxides i.e. additives of the present invention is in the range of from about 200 ppm to 10000 ppm, preferably from about 300 ppm to about 7500 ppm, more preferably from about 400 ppm to about 5000 ppm, most preferably from about 500 ppm to about 2500 ppm. Other total amounts of the alkylene oxides employed in the present invention are, but not limited to, in the lower ppm ranges from about 150 ppm to about 1000 ppm, preferably in the range from about 250 ppm to about 850 ppm, more preferably from about 350 ppm to about 750 ppm, most preferably from about 450 ppm to about 650 ppm in respect to dry mineral matter.

Still further ranges for the alkylene oxides to be employed in total amounts are from about 10 ppm to about 100 ppm, preferably from about 30 ppm to about 80 ppm, more preferably from about 40 ppm to about 60 ppm, still more preferably from about 45 ppm to about 55 ppm, in respect to dry mineral matter. The skilled person will thus also recognize that the ppm values are convertible to wt % values. Thus a workable range of the alkylene oxides of the present invention such as 50 ppm to 5000 ppm is equivalent for the range of 0.005 wt % to 0.5 wt %.

The process for preparing the slurry of mineral matter of the present invention is performed at a temperature in the range of from about 5° C. to about 100° C., preferably in the range from about 15° C. to about 80° C., more preferably in the range from about 20° C. to about 60° C., most preferably from about 25° C. to about 50° C. A preferred ambient temperature being 23° C., with possible deviations of ±3° C., being applicable to the ambient temperature as well as to the ranges just mentioned above.

The molecular weight of the alkylene oxides of the present invention can be readily determined by the skilled man using e.g. Gel Permeation Chromatography (GPC), as described in WO/2010/072769, and according to DIN 55672-1. For calibration, polyethylene glycol standard, analytical standard set $M_p$ 400-40000 from Fluka (product number 81396) was used. The ratio of the EO/PO can be determined according to $^1$H-NMR (proton nuclear magnetic resonance) as disclosed in WO/2010/072769.

Thus the process of whitening of mineral mater slurry surface of the present invention is characterised in that said process comprises the following process steps:
  (a) preparing by dispersing and/or grinding at least one water based mineral matter slurry
  (b) adding during and/or after step a) 0.005 wt % to 0.5 wt % in respect to dry mineral matter of at least one ethylene oxide and/or propylene oxide and/or butylene oxide block copolymers,
  (c) optionally adding 0.005 wt % to 5 wt % in respect to dry mineral matter of at least one dispersing and/or grinding aid during and/or after step (a) and/or step (b)

The mineral matter slurry of the present in invention has a solids content of at least 5 wt %, preferably 50-80 wt %, more preferably 70-79 wt %, most preferably 72-78.5 wt % based on dry mineral matter. Higher solid contents such as 82 wt % based in dry mineral matter can be achieved by up concentrating the aqueous based mineral matter slurry. Such upconcentrating methods being known to the skilled person, such as thermal or mechanical upconcentration.

The invention is now further described by the following examples which are of an illustrative character, but in no way are meant to restrict the invention to the exemplified embodiments. The examples show the whitening of the surface of a mineral matter slurry according to the process of the present invention compared to prior art.

EXAMPLES

The following non-limitative examples are intended to illustrate certain embodiments of the invention and should not be construed to limit the scope of the invention as set out in the claims.

Experimental Set-Up

| Sample preparation | 500 ml bottle |
|---|---|
| Slurry quantity | 500 g |
| Shaken for (min) | 5 min |
| Container to make the surface picture | Crystallising dish 60 mm × 115 mm (height × diameter) |

Illumination

| Eclectic lighting | Kaiser Repro RB 5055HF |
|---|---|
| Angle (in air relative to liquid surface) | 40° from liquid plane |
| Power | Level 4 |
| Distance to the slurry surface | 40 cm |

Imaging

| Camera | Canon PowerShot A640 (1/1.8 inch CCD sensor) |
|---|---|
| Camera Objective | Focal length 7.3-29.2 mm, aperture range 1:2.8-4.1 |
| Resolution (pixel × pixel × bit depth) | 2'272 × 1'704 × 24 |
| Zoom (×magnification) | 1 |
| Distance to slurry surface | 11 cm |
| Shutter speed | 1/50 s |
| Image format | JPEG |
| Image acquisition | 90° (perpendicular) to the slurry surface plane |

Software

| Frame grabber | ImageAccess Performance class: Enterprise, ver. 8, of Imagic Bildverarbeitung AG |
|---|---|
| Image analysis | analySIS ver. 3.1 (build 540) from Olympus SoftImageSolutions GmbH |
| Image editing tool | Corel X4 Photo-Paint |
| Edited resolution (pixel × pixel × bit depth) | 1'500 × 1'200 × 24 |

Material
Additives
Prior Art
1) Polyethylene glycol Mw 600, CAS 25322-68-3
2) 2-Amino-2-methyl-1-propanol, CAS 124-68-5
Invention
3) Triblock PEG250-PPG1800-PEG250 (31PO/11EO)
4) Dowfax 63 N 30, DOW
5) Dowfax 63 N 40, DOW
6) Lumiten P-T, BASF
7) Triblock PEG 300—PPG 1200—PEG 300
8) Triblock PPG 2100—PEG 600—PPG 2100
9) Blend Lumiten P-T/Bevaloid 2565 (2:1 w/w):

| Additive | Chemistry | Properties |
|---|---|---|
| 3) Triblock PEG250-PPG1'800-PEG250 (31PO/11EO) | produced by polymerisation of EO and PO; | |
| 4) Dowfax 63 N 30, DOW | produced by polymerisation of EO and PO | Cloud point: 62° C. (10% surfactant in a solution of 25% diethylene glycol butyl ether in water; Cloud Points: ASTM D 2024) Viscosity (ASTM 445/446): 441 cSt at 25° C. Theoretical Molecular Weight (Molecular Weight: calculated from the molecular weight of the initiator and oxide units in the molecule): 2'400 g/mol |
| 5) Dowfax 63 N 40, DOW | produced by polymerisation of EO and PO | Cloud point: 72° C. (10% surfactant in a solution of 25% diethylene glycol butyl ether in water; Cloud Points: ASTM D 2024) Viscosity (ASTM 445/446): 589 cSt at 25° C. Theoretical Molecular Weight (Molecular Weight: calculated from the molecular weight of the initiator and oxide units in the molecule): 2'800 g/mol |
| 6) Lumiten P-T, BASF | produced by polymerisation of EO and PO | Viscosity (Contraves Rheometer; DIN 53 019 STV, MS 45/II): ~500 mPa · s |

-continued

| Additive | Chemistry | Properties |
|---|---|---|
| 7) Triblock | produced by polymerisation of EO and PO; PEG 300 - PPG 1'200 - PEG 300 | |
| 8) Triblock | produced by polymerisation of EO and PO; PPG 2'100-PEG 600-PPG 2'100 | |
| 9) Bevaloid 2565 | produced by polymerisation of EO and PO | Cloud point: 33-37° C. (10% surfactant in a solution of 25% diethylene glycol butyl ether in water; Cloud Points: ASTM D 2024) Brookfield viscosity at 20° C.: ~800 mPa · s (viscosity measurement The Brookfield viscosity is measured after 1 minute of stirring by the use of a RV DV-III ultra Brookfield ™ viscometer and a rotation speed of 100 rpm (revolutions per minute) with the appropriate disc spindle 4) |

*) PPG: polypropyleneglycol; PEG: polyethyleneglycol

Minerals

Blend of Chinese/Vietnamese/Malaysian Marble (approximately 50:25:25 in respect to dry weight)

HCl insoluble part: 0.25 wt %

Mineralogy of the HCl-insoluble part:

Graphite, Muscovite, Chlorite, Feldspar, Talc, Amphibole, Quartz

All size distribution values were measured with a Sedigraph 5100 particle size analyser from Micrometrics (USA) in an aqueous solution of 0.1 wt % $Na_4PO_7$, wherein the samples are dispersed using a high-speed stirrer and ultrasound. The $d_N$ value being defined as that equivalent spherical diameter under settling below which N % by weight of the material particles are finer. The $d_{50}$ is thus taken to be the weight median particle size.

Preparation of a Mineral Slurry

Dry ground Marble blend, having a $d_{50}$ of 45 µm, is wet ground to a $d_{50}$ of 1.4 µm. The wet grinding is done at 78 wt % solids in tap water in a vertical attritor mill having a volume of 1'500 litres in a continuous mode, using zircon silicate beads of 1-1.5 mm diameter and using 0.63 wt % of a sodium/calcium polyacrylate dispersant having a molecular weight (Mw) of 5'500 and polydispersity of 2.7. The final product further had a $d_{98}$ of 7 µm and a BET specific surface area of 6.7 $m^2/g$ determined according to ISO standard 9277. The test method used was the static volumetric method, with multipoint determination. Degas conditions were 250° C./30 min. The fraction <2 µm was 62 wt %, and the fraction <1 µm was 37 wt %. The final solids was 77.4 wt %.

Preparation of Samples 1-9

For each sample, 500 g of slurry was introduced in an 500 ml PE bottle, 500 mg/kg of additive (additives 1-9) in respect to slurry was added and the closed bottle shaken for 5 min at ambient temperature (23° C.±3° C.).

Sample Measurements

The degree of colour was measured pouring the slurry into a glass receptacle of 60 mm height and 115 mm diameter and taking a photograph of the slurry surface in between 5 to 15 min after pouring the slurry into the glass receptacle. Imaging was performed with a readily available digital camera device, e.g. Canon PowerShot A640 (1/1.8 inch CCD sensor). The picture was taken at a resolution of 2272×1704 pixels with a bit depth of 24, in colour mode, Zoom 1 at a distance of the objective to slurry surface at 11 cm and a shutter speed of 1/50 s. Light conditions were the following as set out in the table of the experimental set up. The photographing setup was protected from ambient light.

Out of the image taken with 2272×1704×24 resolution and bit depth, an image section of 1500×1200×24 resolution was selected and submitted to computational calculation for determining the whiteness value. The "zero whiteness" value was determined from a picture taken with closed objective, i.e. with the protective light tight lid clamped on.

As white standard an image section of a $BaSO_4$ tablet (10 g of $BaSO_4$ powder was used to press a tablet in an Omyapress 2000, said press being commercially available) was taken at a resolution of 2'272×1'704 pixels with a bit depth of 24, in colour mode, Zoom 1 (1× magnification) at a distance of the objective to slurry surface at 11 cm and a shutter speed of 1/50 s, an image section of 1'500×1'200×24 resolution was selected and submitted to the same computational calculation for defining an arbitrary 100% whiteness definition.

The wet surface colours of samples 1-9 where photographed and submitted to computational calculation. The $BaSO_4$ standard having a computational value of 202 was set as 100% of whiteness, the "zero whiteness" value to 0. Non-treated wet slurry surface was photographed as a comparative example.

The results of the images from samples 1-9, the image of non-treated slurry as well as "zero whiteness" and 100% whiteness are shown in Table 1, together with their computational value and normalized values.

TABLE 1 wet surface colour of slurry surface

| | Wet surface colour | |
|---|---|---|
| | software calculated value | normalized |
| Black Standard*[1] | 0 | 0 |
| White standard (BaSO$_4$ tablet)*[2] | 202 | 100 |
| Prior art | | |
| Non treated slurry surface | 194 | 96 |
| 1) Polyethylene glycol Mw 600 | 184 | 91 |
| 2) 2-Amino-2-methyl-1-propanol | 187 | 93 |
| Inventive samples | | |
| 3) | 201 | 100 |
| 4) | 202 | 100 |
| 5) | 202 | 100 |
| 6) | 202 | 100 |
| 7) | 202 | 100 |
| 8) | 199 | 99 |
| 9) | 198 | 98 |

*[1]picture with clamped lid on lens;
*[2]Merck BaSO$_4$ 1.01748.0250 [CAS-No. 7727-43-7] for Brightness Standard DIN 5033 is used for calibration.

The results of Table 1 clearly demonstrate that the inventive additives, the herein described alkyleneoxides, present at a concentration of 500 ppm, improve the surface whiteness of the wet slurry surface by 7-8 points over the prior art, and by at least 4 points over the untreated slurry. If the normalized value is set to 100%, the wet slurry surface values are then 7-8% of improved whiteness of the wet slurry, and 4% over the untreated slurry, respectively.

Thus the wet surface whiteness of the slurry is at least 2% above the whiteness of the same slurry with no alkylene oxide present in the step b) of the above disclosed process. Preferably the wet surface whiteness is 3% above the whiteness of the same slurry with no alkylene oxide present in the step b), more preferably the wet surface whiteness is 4% above the whiteness of the same slurry with no alkylene oxide present in the step b).

Thus the present invention provides for a water based mineral matter slurry with a wet slurry surface whiteness of more than 96%, preferably of ≥97%, more preferably of ≥98%, still more preferably of ≥99%, most preferably of 100%, compared to the BaSO$_4$ standard, meaning thus that the wet slurry surface whiteness of the present invention comprises between more than 96% and less or equal 100% compared to the standard whiteness reference of BaSO4, representing 100% whiteness, when measured according to the measuring method of the present invention.

Meaning thus that the wet slurry surface whiteness of the present in invention is comprised between more than 96% and equal or less than 100% compare to the standard whiteness reference of BaSO$_4$, presenting 100% whiteness, when measured according to the measuring method of the present invention. Thus such values are absolute values in the scale of 0% to 100%.

However, increased whiteness levels are not limited to 2%, 3% or 4%. It will be easily understood by the skilled person, that treated and untreated wet slurry surfaces of mineral materials can have whiteness levels below the mentioned 91% in table 1, compared to the standard whiteness reference of BaSO$_4$. Thus the difference between the whiteness levels of treated and untreated mineral matter slurry can also exceed the 4%, for example 5%-10%.

The method for measuring the wet mineral matter slurry surface whiteness according to the present invention comprises the steps of:

(a) providing a wet mineral matter slurry of the present invention and a white standard
(b) comparing computed digitalized surface images of the wet mineral matter slurry with the white standard The present embodiment for measuring the wet mineral matter slurry surface whiteness is however not to be construed to be of limiting character. It remains within the discretion of the skilled person to choose alternative imaging systems which provide for whiteness values for computational comparison, such as analogue imaging and subsequent digitalization of the images, video capturing and subsequent computational comparative analysis of whiteness values.

"Comparing" in the context of the method of the invention means that a white standard is selected, which not necessarily has to be a specific one such as BaSO$_4$, but can be any one known to the person skilled in the art to be suitable as standard white material, with the provision that the standard white is known and the same for any one of the samples to be compared with each other.

With respect to the term "whiteness", there are several whiteness definitions in the art, such as CIE whiteness, Tappi whiteness, etc., any one of which may be measured according to the method of the present invention, provided that the same whiteness is measured with respect to the samples to be compared with each other.

A particular embodiment of the method for measuring the wet mineral matter slurry surface whiteness according to the present invention comprises the steps of:

(a) preparing a wet mineral matter slurry
(b) providing a suitable receptacle to carry the wet mineral matter slurry of step (a)
(c) taking a photograph of the wet slurry surface
(d) compute the whiteness value of the taken photograph or of a section of the photograph of the wet slurry surface
(e) taking a photograph of a white standard
(f) compute the whiteness value of the taken photograph or of a section of the photograph of the white standard
(g) compute the value of zero-white
(h) provide a scale wherein the computed value of the white standard is set to 100% whiteness and the value of zero-white is set to 0% whiteness
(i) compare the computed whiteness value of step (d) with the provided scale of step (h)

Further to this, it still lies in the discretion of the skilled person that the sequence of the steps of the present method be neither static nor mandatory. Of course, the steps (c) to (h) can be rearranged in such a way that first the white standard is photographed and computed, and the wet mineral matter slurry surface is photographed and computed, followed by comparison with the white standard.

Still the method is not limited to doing the computational analysis subsequent to the imaging. It will be evident to the skilled person that imaging and computational analysis can be performed in different sequences separated in time and place, other than as herein described.

Thus an alternative embodiment of the method for measuring the wet mineral matter slurry surface whiteness according to the present invention comprises the steps of:

(a) preparing a wet mineral matter slurry
(b) providing a suitable receptacle to carry the wet mineral matter slurry of step (a)
(c) taking a photograph of the wet slurry surface and of a white standard (d) compute the whiteness value of the taken photograph or of a section of the photograph of (i) the wet slurry surface and of (ii) the white standard, wherein (ii) can also precede (i)

(e) compute the value of zero-white, wherein (e) can precede the steps of (a)-(d)

(f) provide a scale wherein the computed value of the white standard is set to 100% whiteness and the value of zero-white is set to 0% whiteness (g) compare the computed whiteness value (i) of the step (d) with the provided scale of step (h)

The invention claimed is:

1. A process for improving the whitening of a mineral matter slurry surface by reducing flotation of impurities to the slurry surface which cause darkening of the slurry surface, the process comprising the following steps:
   (a) preparing by dispersing and/or grinding at least one water based mineral matter slurry, wherein the mineral matter comprises calcium carbonate and impurities that can cause darkening of a slurry surface, wherein the impurities comprise one or more oxides, sulphides, silicates, and crystalline and/or amorphous carbon; and
   (b) adding to the slurry during and/or after step a), 0.005 wt % to 0.5 wt %, based on dry weight of the mineral matter, of at least one alkylene oxide block co-polymer or at least one alkylene oxide random co-polymer, to obtain a slurry of mineral matter in which the slurry surface has improved surface whiteness over the same slurry in which the at least one alkylene oxide block co-polymer or the at least one alkylene oxide random co-polymer is not added, wherein the whitening of the slurry surface is improved by reducing flotation of impurities to the slurry surface which cause darkening of the slurry surface.

2. The process according to claim 1, wherein the co-polymer added in step b) is at least one alkylene oxide block co-polymer.

3. The process according to claim 1, wherein 0.005 wt % to 5 wt %, based on dry weight of the mineral matter, of at least one dispersing and/or grinding aid is added during and/or after step a) and/or step b).

4. The process according to claim 1, wherein the at least one alkylene oxide block co-polymer is a bi-block copolymer.

5. The process according to claim 4, wherein the bi-block copolymer is an EO/PO block polymer.

6. The process according to claim 1, wherein the at least one alkylene oxide block co-polymer is a tri-block copolymer.

7. The process according to claim 6, wherein the tri-block copolymer is an EO/PO/EO or a PO/EO/PO block copolymer.

8. The process according to claim 6, wherein the tri-block copolymer has the general structure:

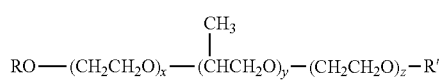

and wherein x, y, and z each independently represents any single integer between, or equal to 1 and 120, and wherein x and z are the same or different integer(s), or

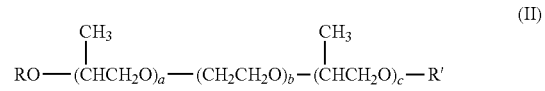

in which a, b, or c each independently represent any single integer between, or equal to 1 and 120, and wherein a and c are the same or different integer(s), and wherein R and R' in formulas (I) - (II) are alkyl residues and/or hydrogen.

9. The process according to claim 8, wherein x, y, and z each independently represent any single integer between, or equal to 1 and 80, and a, b, or c each independently represent any single integer between, or equal to 1 and 80.

10. The process according to claim 8, wherein x, y, and z each independently represent any single integer between, or equal to 3 and 70, and a, b, or c each independently represent any single integer between, or equal to 3 and 30.

11. The process according to claim 8, wherein x, y, and z each independently represent any single integer between, or equal to 5 and 34, and a, b, or c each independently represent any single integer between, or equal to 4 and 34.

12. The process according to claim 4, wherein the bi-block has the general structure:

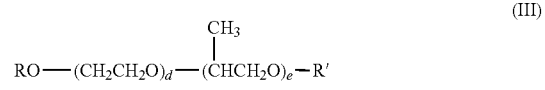

or

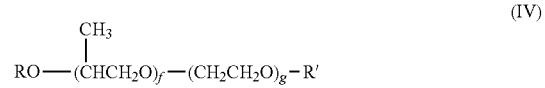

wherein d, e, f or g each independently represent any single integer between, or equal to 1 and 120, d and e are the same or different integer(s), and for g are the same or different integer(s), and wherein R and R' in formulae (III) - (IV) are alkyl residues and/or hydrogen.

13. The process according to claim 12, wherein d, e, for g each independently represent any single integer between, or equal to 1 and 80.

14. The process according to claim 12, wherein d, e, for g each independently represent any single integer between, or equal to 2 and 70.

15. The process according to claim 12, wherein d, e, for g each independently represent any single integer between, or equal to 4 and 40.

16. The process according to claim 3, wherein the at least one dispersing and/or grinding aid is an anionic dispersing and/or grinding aid.

17. The process according to claim 3, wherein the at least one anionic dispersing and/or grinding aid is selected from organic or inorganic dispersing and/or grinding aids.

18. The process according to claim 3, wherein the at least one anionic dispersing and/or grinding aid is an organic dispersing and/or grinding aid selected from the group consisting of sodium citrate, a sodium acrylate, a homo- or copolymer of sodium acrylate or sodium methacrylate, and any combination thereof.

19. The process according to claim 3, wherein the at least one anionic dispersing and/or grinding aid is an inorganic dispersing and/or grinding aid selected from the group consisting of sodium pyrophosphate, sodium polyphosphate, sodium hexametaphosphate and sodium tripolyphosphate.

20. The process according to claim 3, wherein the at least one anionic dispersing and/or grinding aid is an anionic polymeric dispersant selected from the group consisting of polymeric dispersants comprising at least one group chosen form a hydroxyl group, an amido group, a carboxyl group, a sulfo group and a phosphono group, and alkali, earth alkali metal and ammonium and/or amine salts thereof.

21. The process according to claim 20, wherein the anionic polymeric dispersant is a polymeric acrylic dispersant having a molecular weight from 1000 g/mol to 30000 g/mol.

22. The process according to claim 20, wherein the anionic polymeric dispersant is a polymeric acrylic dispersant having a molecular weight from 2500 g/mol to 16000g/mol.

23. The process according to claim 20, wherein the anionic polymeric dispersant is a polymeric acrylic dispersant having a molecular weight from 3200 g/mol to 13000 g/mol.

24. The process according to claim 20, wherein the anionic polymeric dispersant is a polymeric acrylic dispersant having a molecular weight from 3300 g/mol to 7500 g/mol.

25. The process according to claim 20, wherein the anionic polymeric dispersant has acid groups that are partially or fully neutralized, by at least one mono and/or bivalent and/or trivalent and/or tetravalent neutralizing agent.

26. The process according to claim 25, wherein the at least one mono- or bivalent neutralizing agent is lithium, sodium, potassium, magnesium, calcium, ammonium, or any combination thereof.

27. The process according to claim 1, wherein the mineral matter is natural calcium carbonate obtained from one or more of marble, limestone, chalk and calcite.

28. The process according to claim 1, wherein the mineral matter is precipitated calcium carbonate.

29. The process according to claim 1, wherein the mineral matter comprises calcium carbonate and one or more of kaolin, talc, mica, dolomite, bentonite, $TiO_2$ and $Al(OH)_3$.

30. The process according to claim 1, wherein the oxides include iron oxides, the sulphides include iron sulphides and pyrite, and the carbon includes graphite.

* * * * *